(12) United States Patent
Vavroch et al.

(10) Patent No.: US 10,872,385 B2
(45) Date of Patent: Dec. 22, 2020

(54) TIME DATA ANALYSIS

(71) Applicant: CERNER INNOVATION, INC., Kansas City, KS (US)

(72) Inventors: Nathan M. Vavroch, Kansas City, MO (US); Daniel Aycock, Kansas City, MO (US)

(73) Assignee: CERNER INNOVATION, INC., Kansas City, KS (US)

(*) Notice: Subject to any disclaimer, the term of this patent is extended or adjusted under 35 U.S.C. 154(b) by 186 days.

(21) Appl. No.: 15/855,029

(22) Filed: Dec. 27, 2017

(65) Prior Publication Data
US 2018/0122018 A1 May 3, 2018

Related U.S. Application Data

(62) Division of application No. 14/505,695, filed on Oct. 3, 2014, now Pat. No. 10,339,607.

(51) Int. Cl.
*G06Q 40/00* (2012.01)
*G06Q 50/22* (2018.01)
*G16H 10/60* (2018.01)
*G16H 40/20* (2018.01)

(52) U.S. Cl.
CPC ........... *G06Q 40/125* (2013.12); *G16H 10/60* (2018.01); *G16H 40/20* (2018.01)

(58) Field of Classification Search
CPC .............................. G16H 40/20; G16H 10/60
See application file for complete search history.

(56) References Cited

U.S. PATENT DOCUMENTS

| | | |
|---|---|---|
| 2002/0042723 A1 | 4/2002 | Rice et al. |
| 2002/0169637 A1 | 11/2002 | Akers et al. |
| 2009/0089392 A1 | 4/2009 | Fiedotin et al. |
| 2009/0119062 A1 | 5/2009 | Owens et al. |

OTHER PUBLICATIONS

Final Office Action dated Oct. 30, 2017 in U.S. Appl. No. 14/505,695, 11 pages.
Non-Final Office Action dated Jun. 29, 2017 in U.S. Appl. No. 14/505,695, 12 pages.

*Primary Examiner* — Sheetal R Paulson
(74) *Attorney, Agent, or Firm* — Shook, Hardy & Bacon L.L.P.

(57) ABSTRACT

Methods, systems, and computer-readable media are provided for analyzing amounts of time spent in medical records. Time data may be analyzed by clinician, by specialty, by location, by patient, by activity, and the like. Such analysis will provide, among other things, an insight into how much total time is spent in medical records, how the time is spent, when the time is spent, etc. By breaking down the time data it may be possible to identify modifications to reduce the amount of time spent in medical records.

20 Claims, 17 Drawing Sheets

TIME DATA ANALYSIS

CROSS-REFERENCE TO RELATED APPLICATIONS

This application is a divisional of U.S. application Ser. No. 14/505,695, titled "TIME DATA ANALYSIS," filed Oct. 3, 2014, which is incorporated herein by reference in its entirety.

BACKGROUND

Clinicians access electronic medical records (EMRs) multiple times within a given shift of work and even outside of their respective work shifts. The EMRs are accessed to, for example, document patient care, examine patient histories, review medications, prescribe medications, enter orders for a patient, check a status of an order, etc. While the EMR is necessary to provide efficient patient care, if not used properly it may not yield a highest efficiency result or may even reduce efficiency. For example, a clinician that is not properly trained on an EMR system may not document into a chart as quickly as he/she should. Another example may be a department within a healthcare facility that does not have customized software to meet their needs (e.g., an obstetric practice has specific timelines and milestones tracked that are not relevant in, for instance, cardiology, and may require specialized technology to optimize efficiency). Failure to identify such problems may lead to an increase in reduced efficiency and a decline in patient satisfaction and even revenue.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer-readable media for analyzing time spent in, for instance, electronic medical records (EMRs) to identify one or more of clinicians, practice areas, locations, etc. that are spending an amount of time exceeding a predetermined threshold amount of time in an EMR. Further analysis may associate a cost with the amount of time spent in an EMR. The time data may be spliced into one or more categories or activities to further narrow the analysis. Categories may include, for example, clinician categories, location categories, specialty categories, patient categories, and the like. Thus, time data may be spliced to show time data for one individual clinician (i.e., a per-clinician time data level), or one area of practice/specialty, or one particular patient, etc. Activities as used herein, refer generally to one or more actions taken by a user. The actions may be performed while in an EMR. Activities include, but are not limited to, documentation, order entry, chart review, patient history, medication review/entry, and the like. Such splicing or segmentation provides an exact view into the amount of time spent in EMRs.

BRIEF DESCRIPTION OF THE DRAWINGS

Embodiments are described in detail below with reference to the attached drawings figures, wherein.

DETAILED DESCRIPTION

Figure 1:
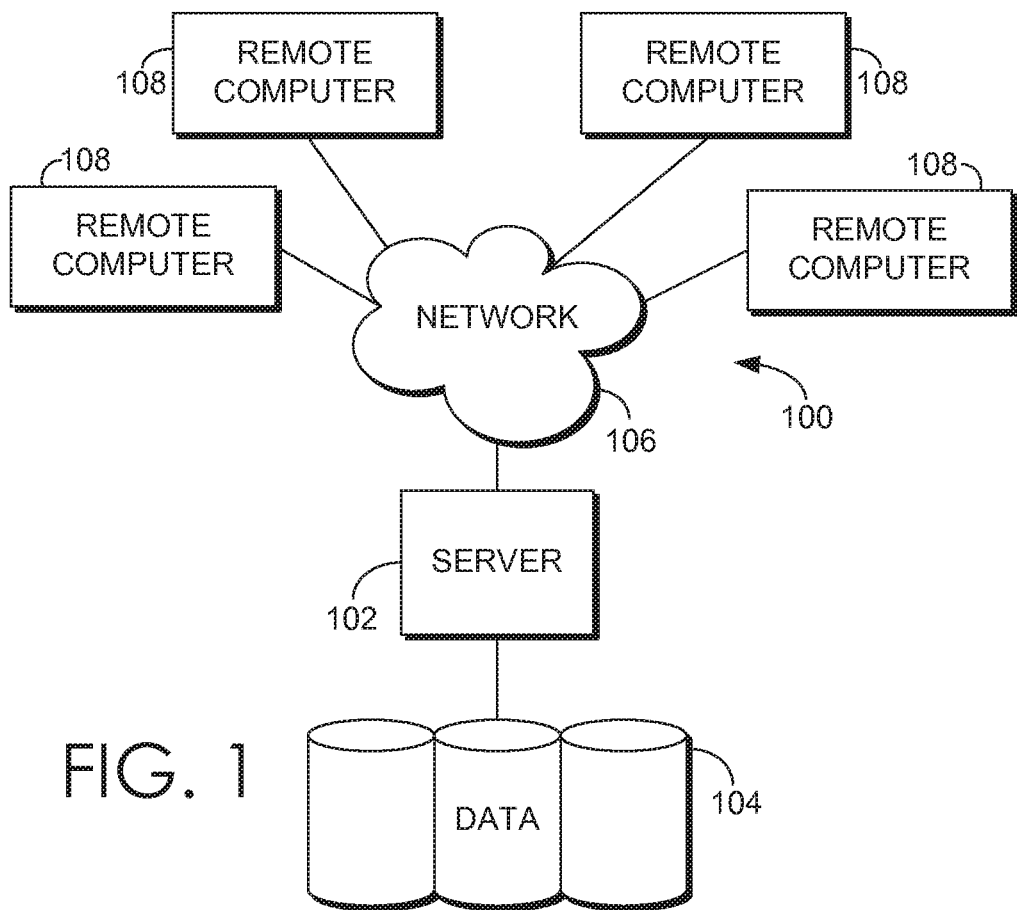
FIG. 1 is a block diagram of an exemplary computing system suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-readable media for analyzing time data. In one aspect, the invention is directed to analyzing time data for time spent in, for instance, electronic medical records (EMRs) to identify one or more of clinicians, practice areas, locations, etc. that are spending an amount of time exceeding a predetermined threshold amount of time in an EMR. Such identification may be helpful to identify problem areas so that modifications may be implemented to try and improve the problem areas (e.g., by reducing the amount of time spent in the EMR). Large amounts of time are required to be spent in patient records due, in part, to the current state of technology in healthcare. However, any improvements to efficiency while in the EMR will only improve clinician efficiency, healthcare facility efficiency, and patient satisfaction.

Further embodiments of the invention perform an analysis to associate a cost with the amount of time spent in an EMR. Such association may provide insight into areas where costs are too high due to, for instance, inefficiency.

To maximize the analysis of the time data, the time data may be spliced into one or more categories or activities to further narrow the analysis. As previously mentioned, categories may include, for example, clinician categories, location categories, specialty categories, patient categories, and the like. Thus, time data may be spliced to show time data for one individual clinician (i.e., a per-clinician time data level), one area of practice/specialty, one particular location, or one particular patient, etc. Activities as used herein, refer generally to one or more actions taken by a user. The actions may be performed while in an EMR. Activities include, but are not limited to, documentation, order entry, chart review, patient history, medication review/entry, and the like. Such splicing or segmentation provides an exact view into the amount of time spent in EMRs.

A first aspect is directed to a computerized method, carried out by at least one server having one or more processors. The method includes, in part, receiving time data, wherein the time data represents a total amount of time spent in one or more electronic medical records (EMRs) by a plurality of clinicians; segmenting the time data to a per-clinician time data level such that the time data illustrates the total amount of time spent in the one or more EMRs by each clinician individually; segmenting the per-clinician time data such that the per-clinician time data illustrates one or more activities performed by each clinician individually while in the one or more EMRs; identifying one or more clinicians associated with a total amount of time spent in the one or more EMRs that exceeds a predetermined threshold amount of time; and identifying one or more recommendations to modify the total amount of time spent in the one or more EMRs by the one or more clinicians associated with the total amount of time spent in the one or more EMRs exceeding the predetermined threshold amount of time.

A second aspect is directed to one or more computer storage media having computer-executable instructions embodied thereon that, when executed, facilitate a method of time data analysis. The media includes receiving time data for a plurality of patients in a facility, wherein the time data represents a total amount of time spent in one or more electronic medical records (EMRs) by one or more clinicians; segmenting the time data to a per-patient time data level such that the time data illustrates the total amount of time spent in each patient's EMR individually; identifying one or more patients associated with a total amount of time spent in their respective EMR that exceeds a predetermined threshold amount of time; and identifying one or more recommendations to modify the total amount of time spent in each patient's EMR of the one or more patients associated with the total amount of time spent in their respective EMRs that exceeds the predetermined threshold amount of time.

A third aspect is directed to one or more computer-readable media having computer-executable instructions embodied thereon that, when executed, facilitate a method of time data analysis. The method includes receiving time data for a facility representing a total amount of time spent in one or more electronic medical records (EMRs) by a plurality of clinicians; segmenting the time data to a per-clinician time data level such that the time data illustrates the total amount of time spent in the one or more EMRs by one or more clinicians; normalizing the time data to identify a normalized time data, wherein the time data is normalized by dividing the total amount of time spent in the one or more EMRs for each clinician of the one or more clinicians by a total number of patients seen by each respective clinician; identifying a system adoption rate for each clinician, wherein the system adoption rate is a percent value representing a percent of work being done by the clinician in the EMR; using the system adoption rate for each clinician, adjusting the normalized time data for each clinician, wherein the adjusting comprises: (1) comparing the system adoption rate for each clinician to a 100% system adoption rate, (2) upon identifying the system adoption rate is lower than 100% system adoption rate, identifying an adjusted time data value for each clinician to adjust the system adoption rate to 100%, and (3) increasing the normalized time data for each clinician to their respective adjusted time data value; using the adjusting time data value for each clinician, identifying one or more clinicians associated with an adjusted time data value exceeding a predetermined threshold amount of time; and identifying one or more recommendations to modify the adjusted time data value for each clinician associated with the adjusted time data value exceeding a predetermined threshold amount of time.

Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer readable media, for instance, database cluster 104. Computer-readable media can be any available media that may be accessed by server 102, and includes volatile and nonvolatile media, as well as removable and non-removable media. By way of example, and not limitation, computer readable media may include computer storage media and communication media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Computer storage media does not comprise signals per se. Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 104, provide storage of computer-readable instructions, data structures, program modules, and other data for the server 102.

The server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home health-care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 108 may also be physically located in non-traditional medical care environments so that the entire health care community may be capable of integration on the network. The remote computers 108 may be personal computers, servers, routers, network PCs, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnection are well known. Accordingly, additional details concerning the internal construction of the server 102 and the remote computers 108 are not further disclosed herein.

Figure 14:
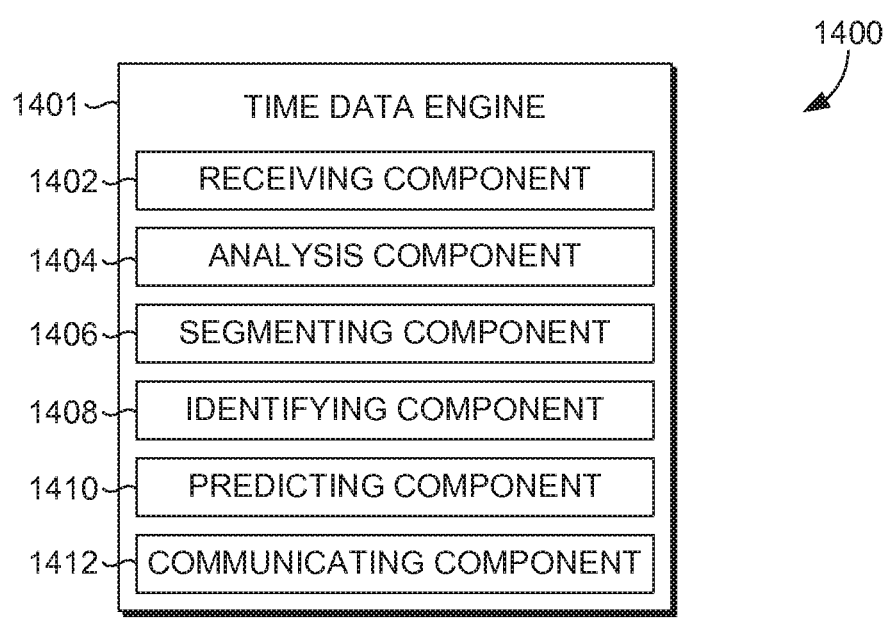
FIG. 14 depicts an exemplary system architecture suitable for implementing embodiments of the present invention.

Turning now to FIG. 14, exemplary system architecture 1400 suitable for implementing embodiments of the present invention is illustrated. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory.

Among other components not shown (including a network, a data base, and a user device, among others), the system 1400 may include a time data engine 1401. The time data engine 1401 may be configured to perform time data analysis. The time data analysis may be performed on any time data received/retrieved by the time data engine 1401. In embodiments, the time data is time data received/retrieved from one or more EMRs. The time data may be received or retrieved from any other source besides an EMR including, but not limited to, a database or any other item to which time data may be tracked. The time data engine 1401 may include a receiving component 1402, an analysis component 1404, a segmenting component 1406, an identifying component 1408, a predicting component 1410, and a communicating component 1410.

The time data engine 1401 may further include timing components (not shown) that monitor time spent in EMRs. For instance, the timing components can distinguish between active time in the EMR and inactive time. Active time, as used herein, refers generally to time spent performing one or more activities and having an active indication no more than a predetermined time interval away from another active indication. Active indications include, but are not limited to, keystrokes (e.g., typing in a keyboard or typing on a touch screen), clicks (e.g., by a mouse), mouse miles (e.g., movement of the mouse), touch screen selections (e.g., any selection of a touch screen), and the like. Thus, a first active indication can be no more than a predetermined time interval away from a second active indication in order to have the time between counted as active time. The timing components may monitor the time intervals and compare to a predetermined time interval to classify time as active or inactive. The timing component may also include metadata tags for each active indication associated with various information including a time stamp for each activity, active indications for each activity, and the like. The metadata tags may also include category tags (indicating a category description) or activity tags (indicating an activity description). For instance, a category tag may identify a particular clinician or area of specialty associated with the active indication. An activity tag may identify the activity performed such as order entry.

Figure 2:
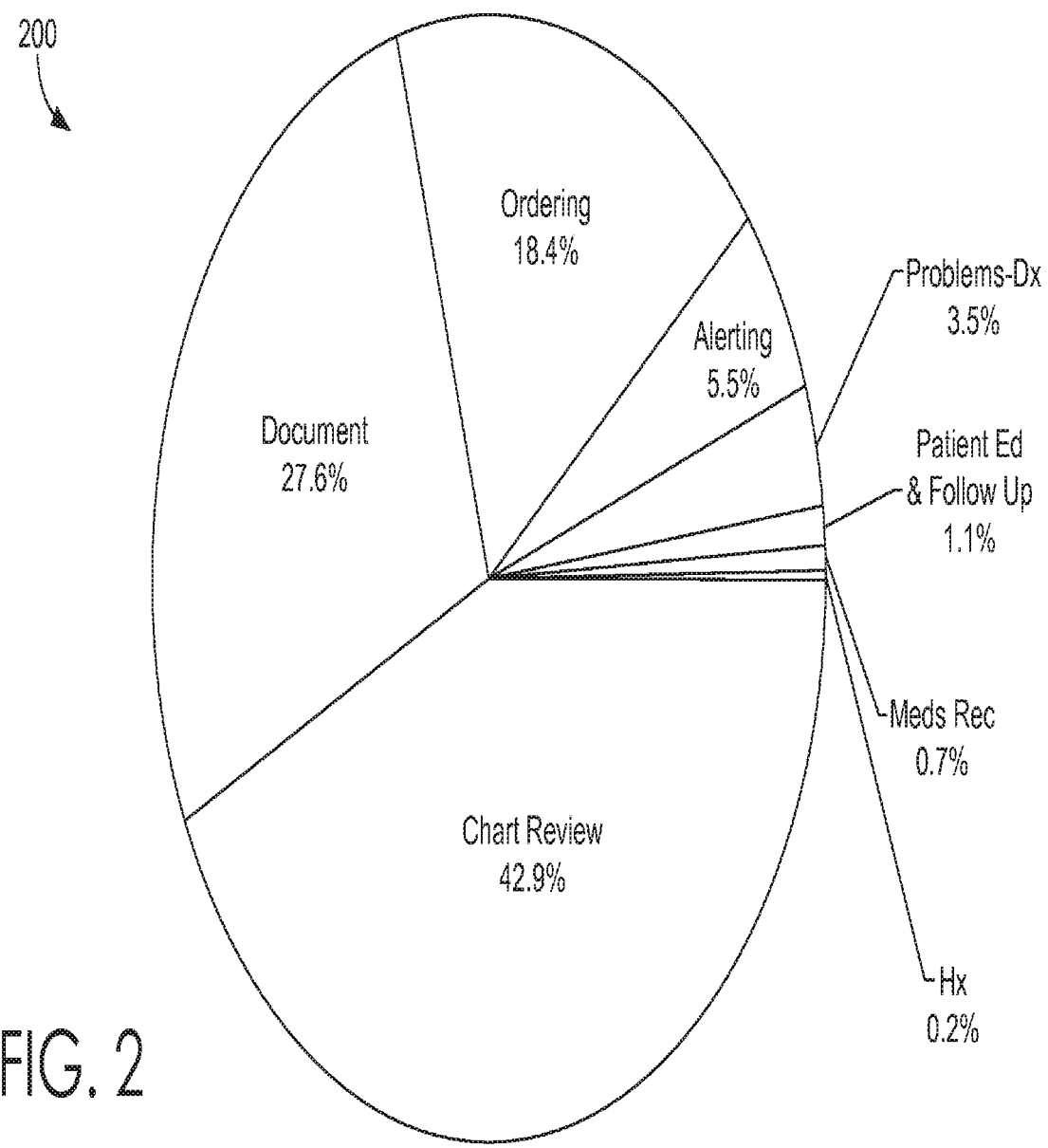
FIG. 2 depicts an exemplary chart illustrating a plurality of activities performed while in a plurality of EMRs.

The receiving component 1402 may be configured for, among other things, receiving (or retrieving) time data. Time data, as used herein, refers generally to a set of data representing a total amount of time spent in one or more EMRs. The total amount of time may be a numerical indication. The time data may be gathered for one or more locations and include multiple categories including, but not limited to, one or more patients, one or more clinicians, one or more areas of practice, and the like. For instance, FIG. 2 provides an exemplary view of a time data summary 200 illustrating how clinicians spend their time. This example was obtained over a period of one day from 178 different clients and includes time data for 87,387 clinicians. FIG. 2 illustrates that in the one day studied, clinicians spent almost half of their time in the EMR reviewing charts. Various other activities are highlighted in the time data summary 200 including documentation, ordering, alerting, and the like. The activities, as previously stated, include one or more actions performed by a user. FIG. 2 also illustrates the capabilities of the time data engine 1401 as to segmenting time data. In this particular time data summary 200 the time data, collecting across multiple clients and multiple clinicians, was compiled and then segmented into a plurality of categories such that an overall view is provided (as opposed to a view regarding a single location or a single clinician).

Figure 3:
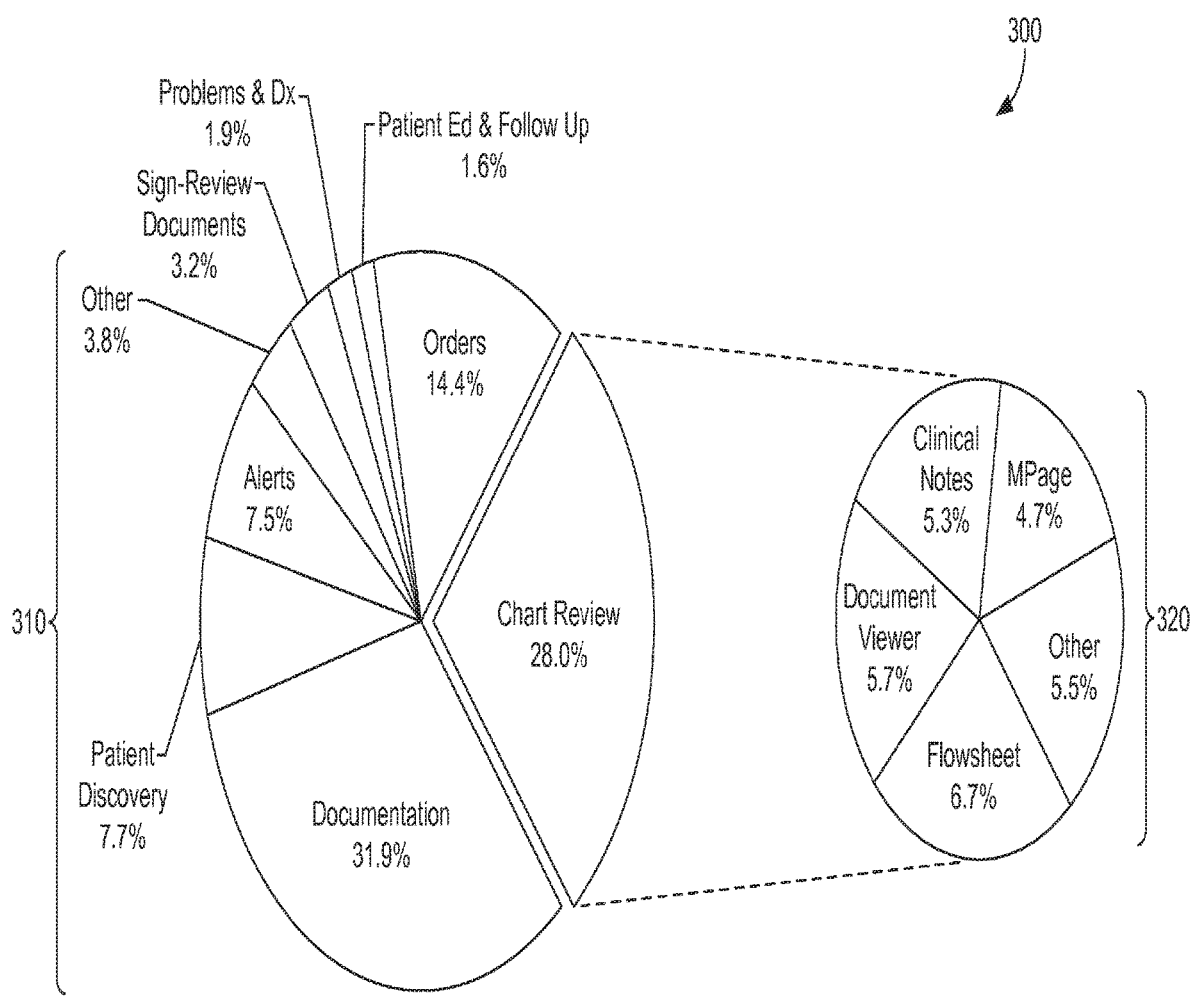
FIG. 3 depicts an exemplary chart illustrating a plurality of activities performed while in a plurality of EMRs further segmented into sub-activities, in accordance with an embodiment of the present invention.

FIG. 3 illustrates additional capabilities of the time data engine 1401 related to segmenting. FIG. 3 provides a view 300 of a time data summary 310 and a segmented time data summary 320. As illustrated, the segmented time data summary 320 has been further broken down into additional activities. As shown, the chart review activity of the time data summary 310 has been broken down into five sub-activities in the segmented time data summary 320. The time data illustrated in FIG. 3 was collected from a single client (i.e., per-location time data level) and includes 3910 clinicians. A view similar to FIG. 3 could be obtained by segmenting the time data summary 200 of FIG. 2 to a per-location time data level.

Returning now to FIG. 14, the analysis component 1404 is configured for, among other things, analyzing the time data. Said analysis may include identifying various categories and activities present within the time data. For instance, in FIG. 2, the analysis component 1404 may compile all of the time data received (by, for example, the receiving component 1402) and identify each category and/or activity present within the time data such that available segmenting options are available to a user. For example, if time data is collected for a practice area that does not include a particular activity, segmenting the time data by that particular activity is not an option. Thus, the analysis component 1404 may sort through and organize time data.

The segmenting component 1406 may be configured for, among other things, segmenting time data into segments based on, for instance, categories, activities, and the like. Categories include clinician categories, patient categories, location categories, specialty categories, and the like. A clinician category, as used herein, refers generally to a category of time data that is broken down (segmented) to a per-clinician time data level. For example, while FIG. 2 was directed to a multiple clients and multiple clinicians, the same type of summary may be offered for a single clinician. In fact, a single clinician included in the time data summary 200 of FIG. 2 may be identified and that data may be segmented for the identified clinician.

A patient category, as used herein, refers generally to a category of time data that is broken down (segmented) to a per-patient time data level. In this embodiment, time data is collected as it pertains to a single patient. One or more clinicians may be included in the time data. The patient category provides an opportunity to identify time data trends for one or more patients or types of patients (e.g., cardiac patients, maternity patients, etc.). This could, in turn, identify patients or types of patients that require more time than others, for instance. Patients, as used herein, refer generally to a unique individual that is seen in a predetermined time period (e.g., a day) and is only counted once in the predetermined time period. For instance, a patient that is hospitalized from Sep. 1, 2014 to Sep. 10, 2014 is counted as a patient each day (assuming one day is the predetermined time period) but is not counted each time within a day that the patient is seen.

A location category, as used herein, refers generally to a category of time data that is broken down (segmented) to a per-location time data level. A location may be a facility (e.g., Hospital A or Hospital B) or a department/area within a facility (e.g., Emergency Department of Hospital A). Locations may also include patient rooms, regions of a facility (e.g., floors 1-10 of a facility), and the like. FIG. 3, as mentioned above, is providing time data for a single location.

The location category may also include time data that is segmented to a per-venue time data level. A venue, as used herein, refers generally to different venues of care including, but not limited to, emergency, inpatient, outpatient, etc. The time data may be segmented by the venue in which the care is provided. For instance, an OB/GYN physician may work in the same facility all day long but would work across multiple venues of care: emergency (e.g., unscheduled delivery), inpatient (e.g., scheduled delivery), and outpatient (e.g., follow-up visits).

Figure 5:
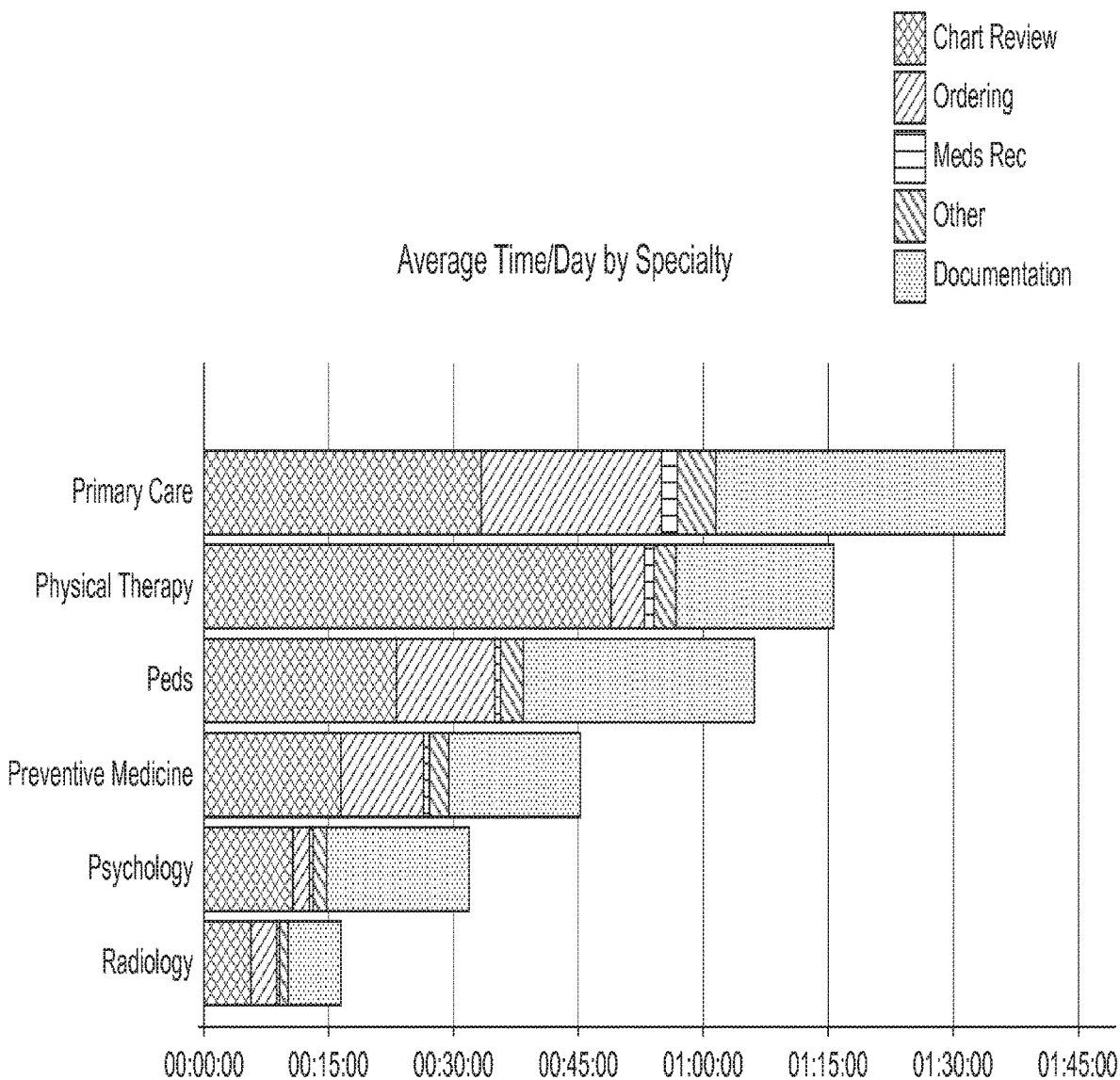
FIG. 5 depicts an exemplary per-specialty time data summary, in accordance with an embodiment of the present invention.

A specialty category, as used herein, refers generally to a category of time data that is broken down (segmented) to a per-specialty time data level. A specialty, as used herein, refers generally to a clinical area of practice such as cardiology, obstetrics, pediatrics, radiology, etc. A per-specialty time data level is provided in FIG. 5. As shown, time data may be broken down per specialty and, in FIG. 5, includes primary care, physical therapy, pediatrics (peds), preventative medicine, psychology, and radiology. The time data may be broken down by several categories and/or activities or a combination thereof. FIG. 5 illustrates this as each specialty category is further broken down into activities (e.g., chart review, ordering, etc.). This illustrates how time data may be used to identify time data trends among specialties. This time data indicates that primary care clinicians spend much more time, on average, in EMRs than radiology clinicians.

Figure 4:
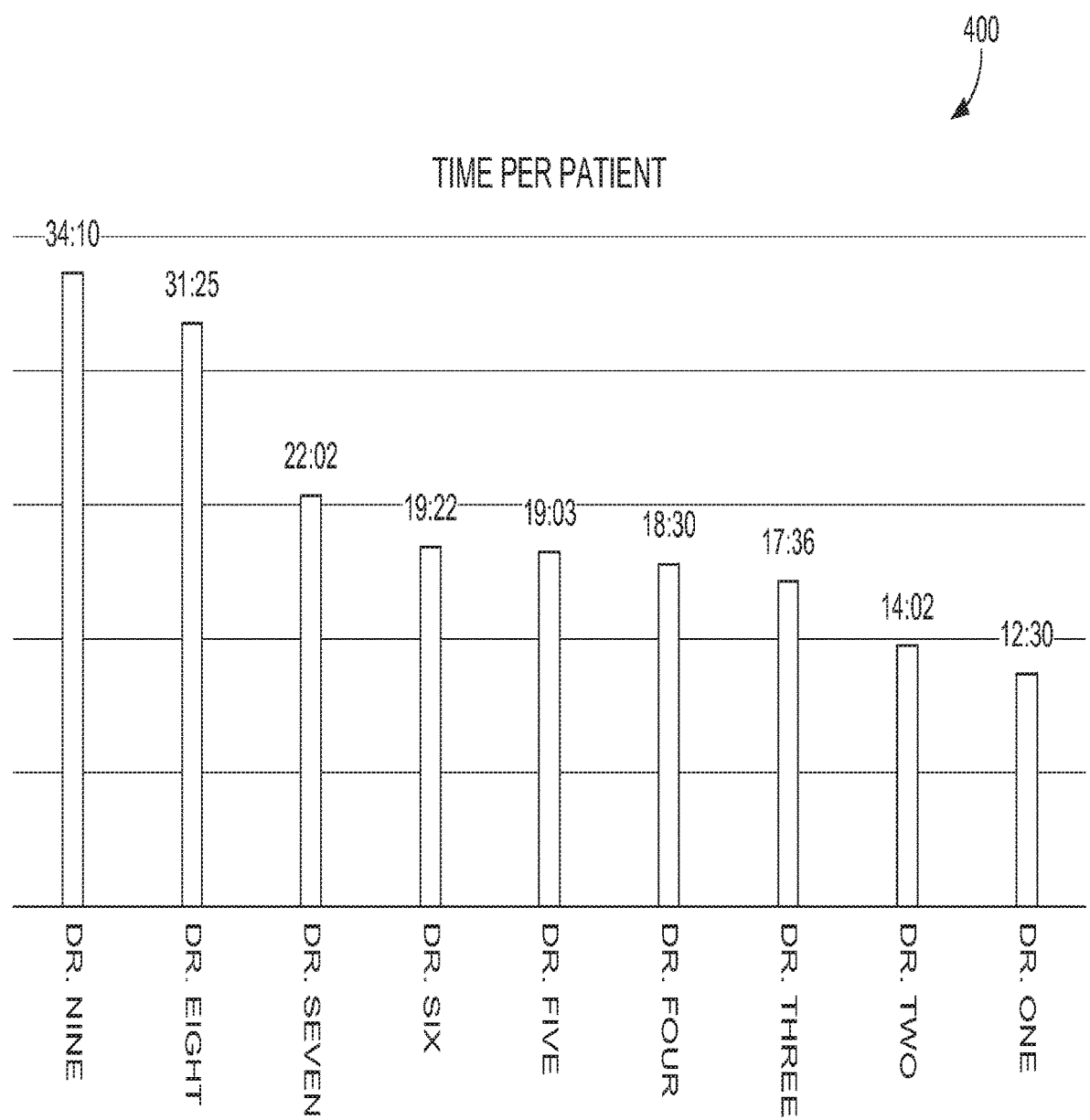
FIG. 4 depicts an exemplary clinician comparison summary, in accordance with an embodiment of the present invention.

In addition to segmenting time data, embodiments of the invention are directed to comparisons using time data. FIG. 4 illustrates an exemplary clinician comparison summary 400. FIG. 4 is a comparison of nine clinicians (e.g., physicians) from a single client that share a common area of specialty and use a same version of the EMR. The time data is broken down into a per-clinician time data level to illustrate the comparison of how long it takes on average for a physician to interact with the EMR per patient seen. It could be broken down into any other appropriate category/activity. For instance, time data could be broken down by activity, such as documentation or ordering, so that it can be viewed what is done most often in the patient's EMR (by one or more clinicians). In FIG. 4, it is clearly seen that Dr. Nine takes much more time interacting with the EMR than does, for example, Dr. One. This may be used as a tool to further review the activity of Dr. Nine or to identify certain patient features or EMR-related features that Dr. Nine may be struggling with. Ultimately, FIG. 4 illustrates a comparison embodiment of the present invention where the system can compare how long it takes clinicians to interact with an EMR on a normalized time per patient basis (i.e., total time divided by total patients).

In an embodiment, the system divides the active time spent in the EMR per clinician by the number of patients seen. This calculation allows comparison of clinicians with varying patient volumes to identify, on average, how much time clinicians are taking per patient. This concept can be extended to account for varying levels of adoption of system use for two key categories: ordering and documentation. Physicians will, often times, have their nurse or other person place orders or document on their behalf. In such cases, the physician logs less time in the EMR because someone else is doing the work for them in the EMR. In those cases, the system may adjust the appropriate category of time to account for the lower use of the system. An algorithm is used by the system to take into account a clinician's current time ordering and/or documenting and adjusts the time up based on how much they did that particular function. This metric may be referred to as "adoption-adjusted time in EMR per patient" and it may be used to identify outliers when comparing clinicians within a given specialty.

As an example, assume Clinician A is only documenting in the system 21.57% of the time at 2 minutes and 50 seconds and is only ordering 20.85% of the time at 41 seconds. Clinician A's time may be written up from 2 minutes and 50 seconds to 6 minutes and 18 seconds to estimate time documenting at 100%. Similarly, the ordering time may be written up from 41 seconds to 1 minute and 32 seconds to estimate time ordering at 100%. At this point, Clinician A may be compared to any other clinician since the system has accounted for differences in patient volume and his/her adoption of the system's functionality.

Returning now to FIG. 14, the identifying component 1408 may be configured for, among other things, identifying one or more time data issues. A time data issue, as used herein, refers generally to a category or an activity that is associated with an amount of time in an EMR that exceeds a predetermined amount of time or a recommended amount of time. For example, clinicians that are associated with an amount of time in an EMR that exceeds a predetermined amount of time may be identified as a time data issue. Time data issues may also be patients, locations, areas of specialties, documentation, order entry, and the like. As a further example, an area of specialty (e.g., radiology) may be identified as spending an amount of time exceeding a recommended amount of time in an EMR. The identified time data issues may be sent to a user in, for an example, an alert, a notification, or the like. The notification may be in the form of an e-mail message, a text message, a notification indicator in a user interface, or the like.

Figure 6:
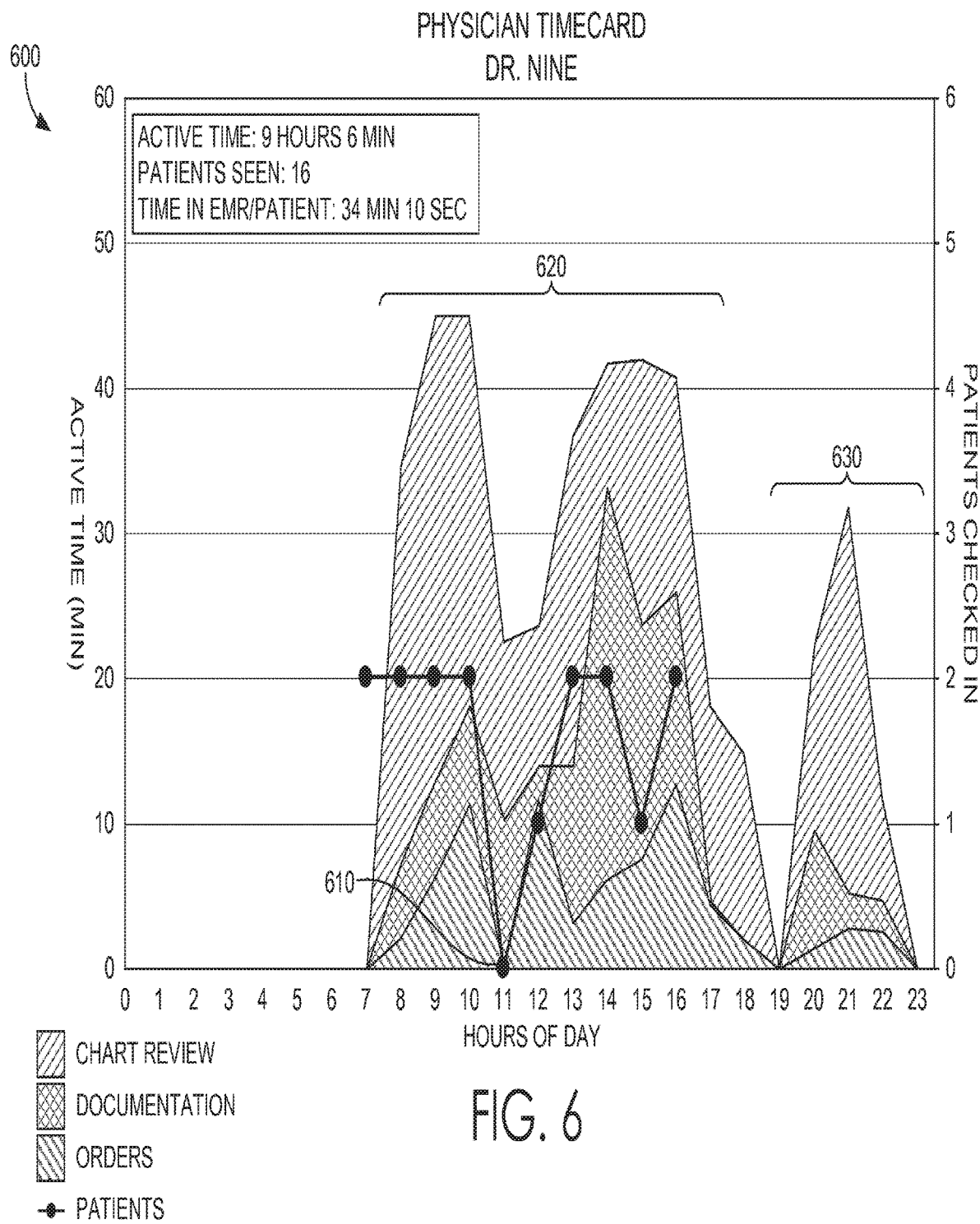
FIG. 6 depicts a per-clinician time data summary, in accordance with an embodiment of the present invention.

As described above with reference to FIG. 4, Dr. Nine was previously identified as a time data issue (as Dr. Nine was spending much more time in the patient's EMR than other clinicians). FIG. 6 illustrates a further segmented view 600 for only Dr. Nine. This view 600 includes an indication of total active time, a total number of patients seen, and a total time in EMR per patient. This information is further divided into activities (e.g., chart review, orders, documentation, etc.) and placed over the hours of the day (x axis). In addition to Dr. Nine spending too much time in EMRs, this view 600 further illustrates that Dr. Nine is also spending time outside of an assigned shift in EMRs. Portion 620 indicates the hours Dr. Nine is on-duty while portion 630 indicates the hours Dr. Nine is off-duty. It may not be desirable for clinicians or clients to spend excessive amounts of time in EMRs after expiration of a shift. Thus, the view 600 indicates that not only is Dr. Nine spending too much time in EMRs but Dr. Nine is not efficient enough to do everything required within a predetermined period of time (i.e., a work shift).

Figure 7:
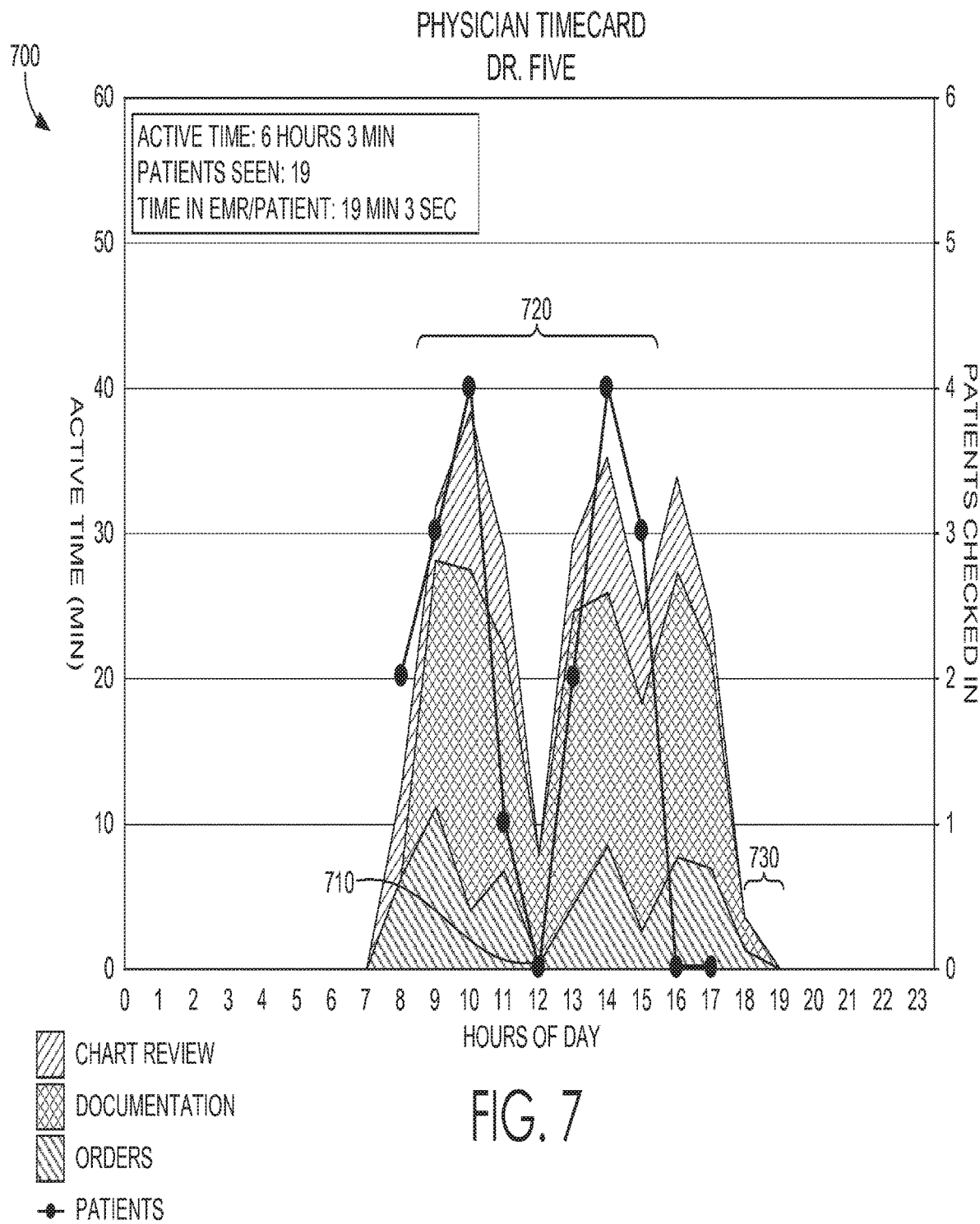
FIG. 7 depicts a per-clinician time data summary, in accordance with an embodiment of the present invention.

FIG. 7 is provided to show a comparison of clinicians as this is an analysis of Dr. Five. The view 700 provides a further segmented view 700 for only Dr. Five. This view 700 includes an indication of total active time, a total number of patients seen, and a total time in EMR per patient. This information is further divided into activities (e.g., chart review, orders, documentation, etc.) and placed over the hours of the day (x axis). This view 700 illustrates that Dr. Five is very efficient as the time in EMR directly corresponds to the number of patients that are checked in there is minimal time spent in EMRs after the predetermined time period as indicated by portion 720 (the work shift) and portion 730 (the off duty time).

This data could be compiled in various formats and presented to a user differently. For instance, data could be compiled for the same set of clinicians illustrated in FIG. 4 but focused on the amount of time spent in EMRs outside of business hours. The below table illustrates data compiled for nine clinicians of a family medicine practice (i.e., single client) over the course of five business days. As illustrated below, Dr. Nine has a very high percentage of time spent in EMRs that is outside of business hours. Dr. Nine may be identified as a time data issue based on the below time data and one or more recommendations may be provided to improve performance of Dr. Nine.

TABLE 1

| USER | % OUTSIDE HOURS |
| --- | --- |
| Dr. Nine | 26.1% |
| Dr. Eight | 24.9% |
| Dr. Four | 13.2% |
| Dr. Seven | 11.2% |
| Dr. Six | 4.3% |
| Dr. One | 3.7% |
| Dr. Two | 2.2% |
| Dr. Five | 0.6% |
| Dr. Three | 0.0% |

Figure 8:
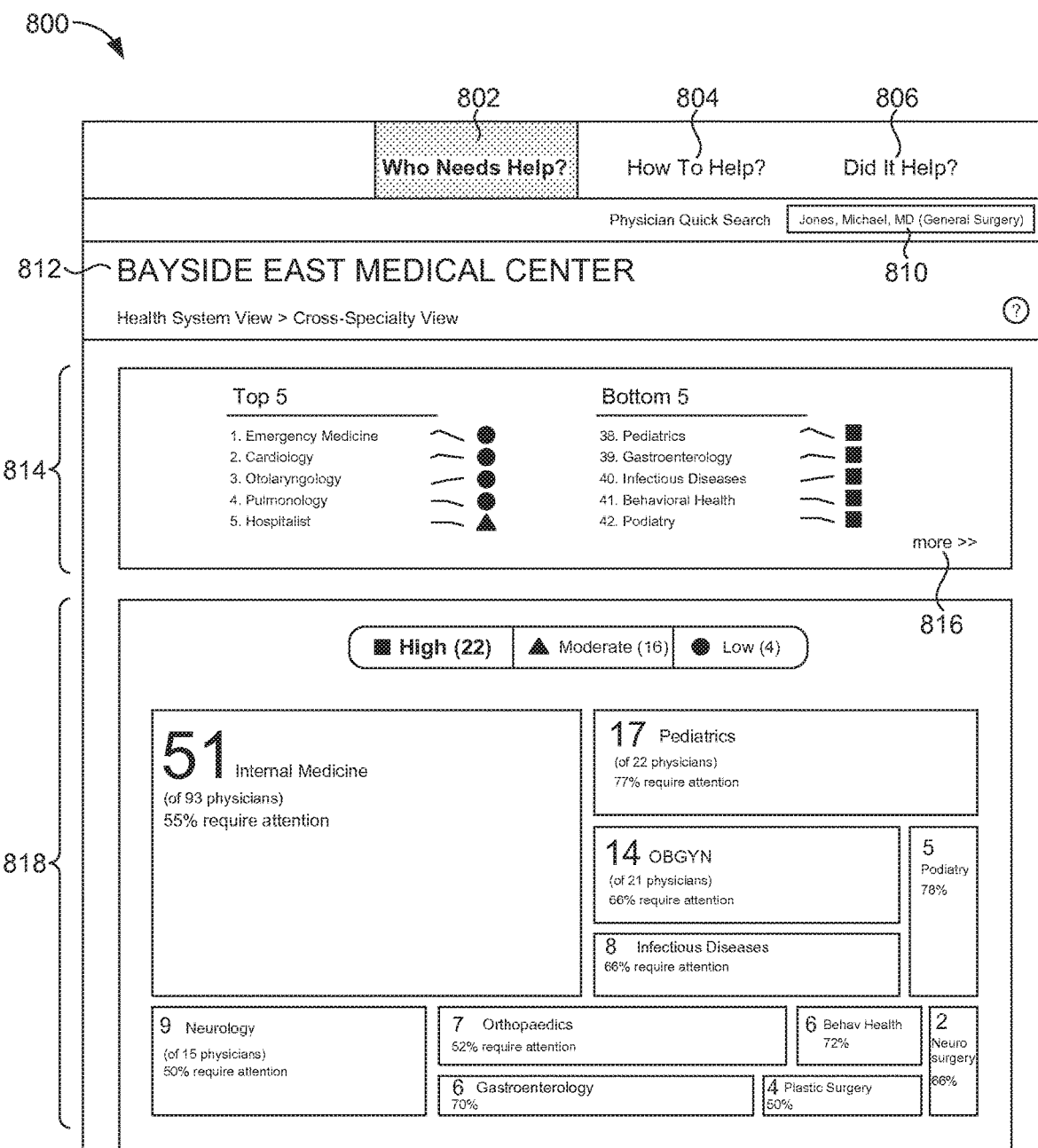
FIG. 8 depicts an exemplary graphical user interface (GUI) illustrating identifying time data issues, in accordance with an embodiment of the present invention.

Once the identifying component 1408 has identified one or more time data issues, the time data issues may be communicated to a user (via the communicating component 1412) and displayed. The results or time data issues may be presented to a user in a graphical user interface (GUI) customized for time data analysis. An exemplary user interface 800 is provided in FIG. 8. FIG. 8 includes a time data issue indicator 802, a recommendation indicator 804, and a results indicator 806. The time data issue indicator 802 is configured such that selection thereof navigates a user to a GUI, similar to that illustrated in FIG. 8, indicating one or more time data issues. The exemplary GUI 800 further includes a search area 810 where a user may search for a specific clinician as they relate to time data, a location area 812 including an indication of a location. The area may also include a breakdown of the segments included in the time data. For instance, GUI 800 illustrates the current view is customized to a per-location time data level and then a per-specialty time data level (as indicated by the "Health System View >Cross-Specialty View" navigation indicator). The GUI 800 may further include a time data results area 814 that displays at least any time data issues identified. The time data results area 814 may also include those categories or activities that performed well in the time data analysis. That is, those categories or activities associated with an amount of time less than a predetermined amount of time are said to perform well. An expansion indicator 816 may also be featured and configured such that selection thereof expands the view of the time data results area 814. A time data issues area 818 is further included and illustrates one or more time data issues. The time data issues area 818 of FIG. 8 is segmented by practice area and then by clinician. For instance, the time data issues area 818 indicates that 51/93 physicians in the internal medical group require attention. The time data issues displayed in the time data issues area 818 of FIG. 8 are those that are associated with a high level of attention required. Further time data issues may be viewed by selecting a moderate indicator or a low indicator.

Once time data issues are identified, the identifying component 1408 may be further configured to identify one or more modifications or recommendations to modify or improve the time data issue. For instance, if a time data issue is a clinician spending too much time in EMRs, the identifying component 1408 may identify one or more recommendations to improve the clinician's performance such as specialized training. Such recommendations may be presented in a GUI such as GUI 900 of FIG. 9. As illustrated in GUI 900, the time data issue indicator 904 and the results indicator 906 are present as well as the recommendation indicator 902 (currently selected).

Figure 9:
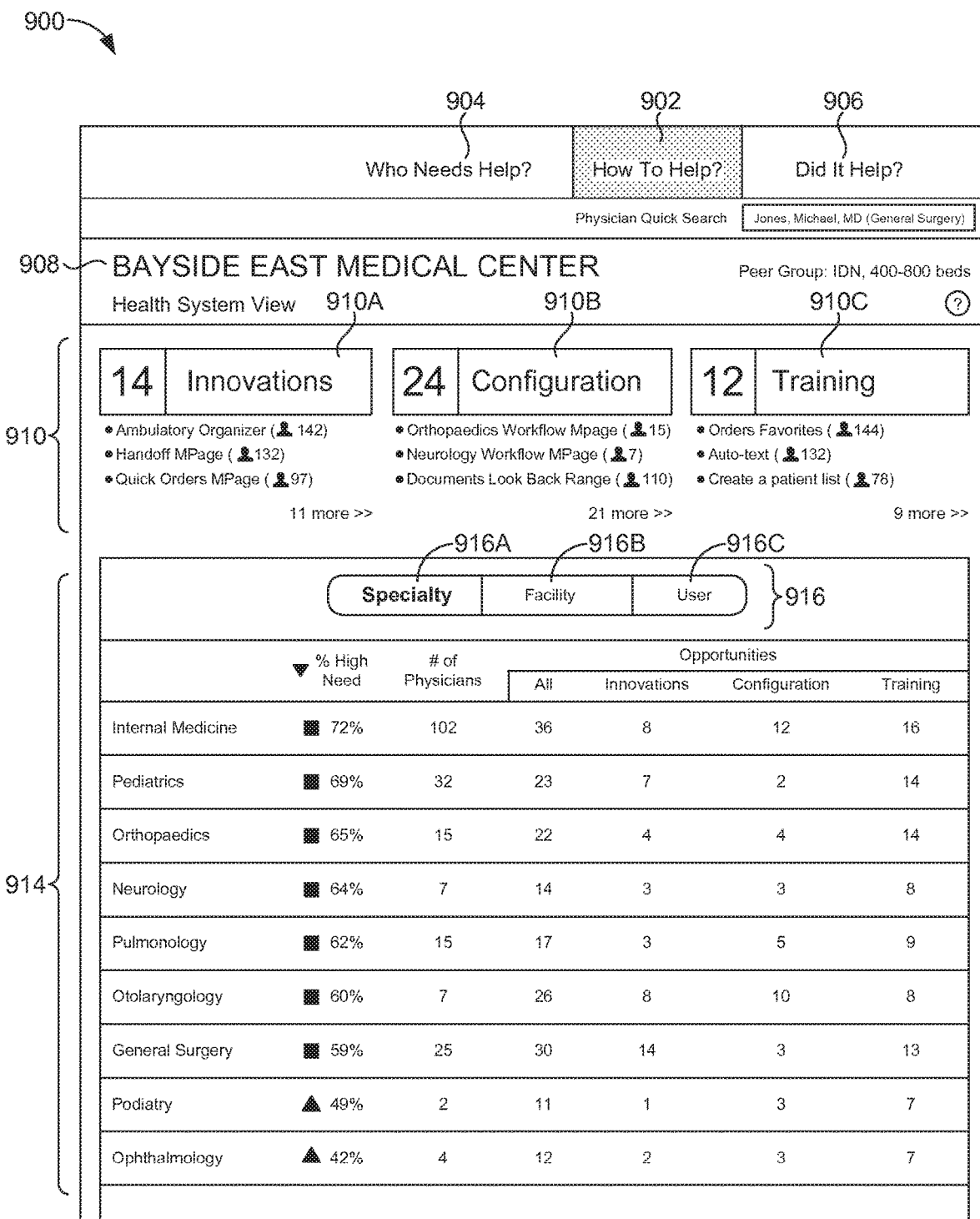
FIG. 9 depicts an exemplary recommendation GUI, in accordance with an embodiment of the present invention.

The recommendation indicator 902 is configured such that selection thereof navigates a user to a GUI similar to that of FIG. 9 that indicates one or more recommendations. The GUI 900 includes a recommendation summary area 910 that includes one or more recommendations. Recommendations may be broken down into several categories such as innovation, configuration, training, and the like. Innovation recommendations may be described as recommendations to implement a new action including, but not limited to, a new code or software. For example, if a particular practice group is exceeding a predetermined amount of time and is identified as a time data issue, the identifying component 1408 may identify that the practice group does not have a particular piece of system functionality installed and recommends installation (of a new, not previously installed, piece of functionality).

In contrast, configuration recommendations may be described as modifications to existing technology. For instance, in the above example, assume that the practice area does have the system functionality installed but they need a specialized view to optimize efficiency. This would be a modification to existing technology and categorized as a configuration recommendation.

Training recommendations include any training sessions that may be recommended including educational information associated with the time data issue or improvement thereof. Training may be recommended based on a comparison of time data with predefined thresholds included in training recommendations or comparison to other users of the same specialty category. The predefined thresholds may be user defined and customized for unique needs.

The GUI includes an innovations indicator 910A, a configuration indicator 910B, and a training indicator 910C. Selection of any one of the innovations indicator 910A, the configuration indicator 910B, or the training indicator 910C may result in a display of one or more recommendations in that category. Alternative, and as illustrated in FIG. 9, a summary of one or more recommendations for each category may be included in proximity to the respective indicator. For example, "create a patient list" is listed as a potential training recommendation near the training indicator 910C.

The GUI 900 further includes an opportunity area 914 illustrating one or more categories for which opportunities or recommendations exist. The opportunity area 914 includes filter area 916 including a specialty indicator 916A (currently selected), a facility indicator 916B, and a user indicator 916C. Selection of any one of the specialty indicator 916A (currently selected), the facility indicator 916B, or the user indicator 916C may result in a filtered view of opportunities associated with the selected filter. For example, in FIG. 9, the specialty indicator 916A is selected so the opportunity area 914 displays a plurality of specialty groups (e.g., internal medicine, pediatrics, orthopaedics, neurology, podiatry, etc.) and opportunities associated therewith. For instance, with respect to internal medicine, a number of physicians (either total included in time data or a number that are identified as time data issues) is displayed as well as opportunities divided by category such that all opportunities (total of 36) are displayed as well as innovation opportunities (8), configuration opportunities (12), and training opportunities (16) being individually displayed.

Figure 10:
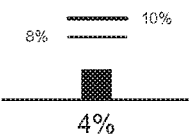
FIG. 10 depicts an assignment GUI, in accordance with an embodiment of the present invention.

Upon displaying the one or more recommendations, one or more recommendations may be assigned to, for example, a clinician, a facility, a specialty group, etc. FIG. 10 provides an exemplary GUI 1000 illustrating assigning a training recommendation to a clinician. The time data issue indicator 1002 is currently selected and a particular clinician 1004 has been selected. An assignment tool 1008 is displayed where time data for the clinician 1004 is displayed and one or more recommended actions are displayed. One of more of the recommended actions may be selected to be assigned to the clinician 1004. In this example, "How to Use a Pre-completed Note" training is selected to assign. Furthermore, a metric goal may be assigned such that progress is monitored. Once the recommendation is selected and a goal is set, a user may select an assign indicator 1006 to assign the recommendations to the clinician 1004. Additional feedback may be monitored such as satisfaction level, receptivity (to training), etc. A notes area 1010 may also be presented with a follow up indicator 1012 indicating when follow up should be performed. Upon completion a save indicator 1014 may be selected to save the assignment.

The satisfaction and receptivity indicators may be valuable in tracking engagement with clinicians throughout training. This may facilitate training coverage (via notes sections), physician sentiment and willingness to engage. This feedback may be useful in customizing future training sessions.

Figure 11:
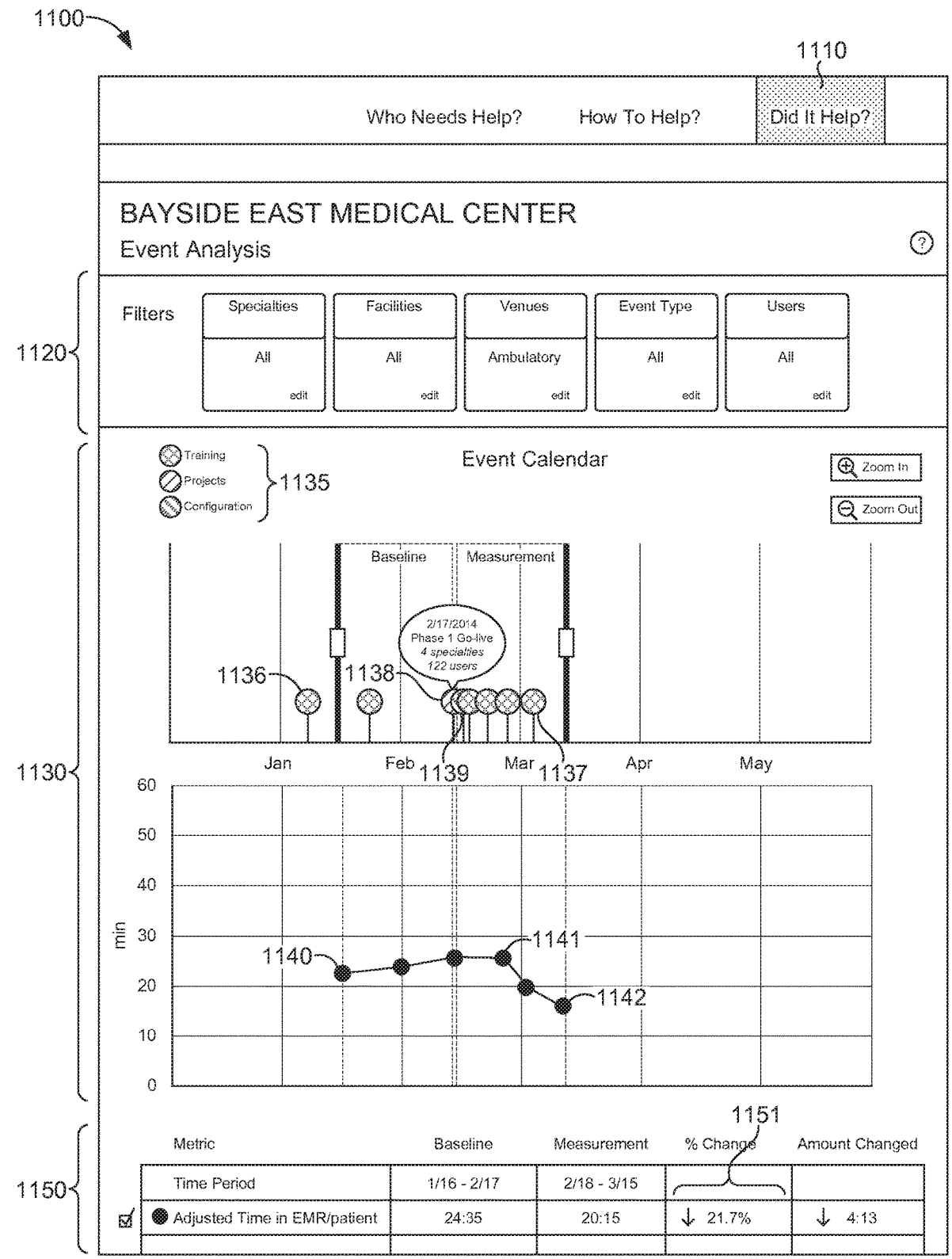
FIG. 11 depicts a results GUI, in accordance with an embodiment of the present invention.

An exemplary implementation is illustrated in FIG. 11. FIG. 11 provides an exemplary GUI 1100 that includes a results indicator 1110 (currently selected) and a filter area 1120 including one or more filters by which the time data has been filtered. In this illustration, the filter has been set to a specific location or venue of care—ambulatory. An events area 1130 includes an events legend 1135 indicating one or more events (recommendations) that are to be implemented. For example, event 1139 is a configuration event while event 1137 is a training event. Indicators 1140, 1141, and 1142 indicate an amount of time in EMRs relative to event 1139, the event that has been selected for evaluations. For example, indicator 1140 is a measure of the amount of time in EMRs prior to event 1139 while indicator 1141 is a measure of time spent in EMRs after the configuration event 1139. As may have been intended, the amount of time spent in EMRs decreased as the configuration event 1139 was implemented. This could potentially be matched up with a predicted improvements area (not shown). Once recommendations are made and implemented, the predicting component 1410 may identify projected improvements. For instance, based on the implemented recommendation, the predicting component 1410 may identify a measurable improvement such as a reduction in an amount of time spent in EMRs. By overlaying the predicted results with the actual results of FIG. 11, it may be beneficial to identify other issues, additional opportunities (e.g., more training sessions may have been beneficial), etc. When result data is received, it may be compared to predicted improvements and, based on the comparison, additional modifications may be required if the updated result data is still exceeding a predetermined amount of time in an EMR.

The results of FIG. 11 (and the implementation of modifications) may be illustrated in a results area 1150. As is shown, the EMR time change indicator 1151 indicates a reduction in the amount of time spent in EMRs by 21.7%.

Figure 12:
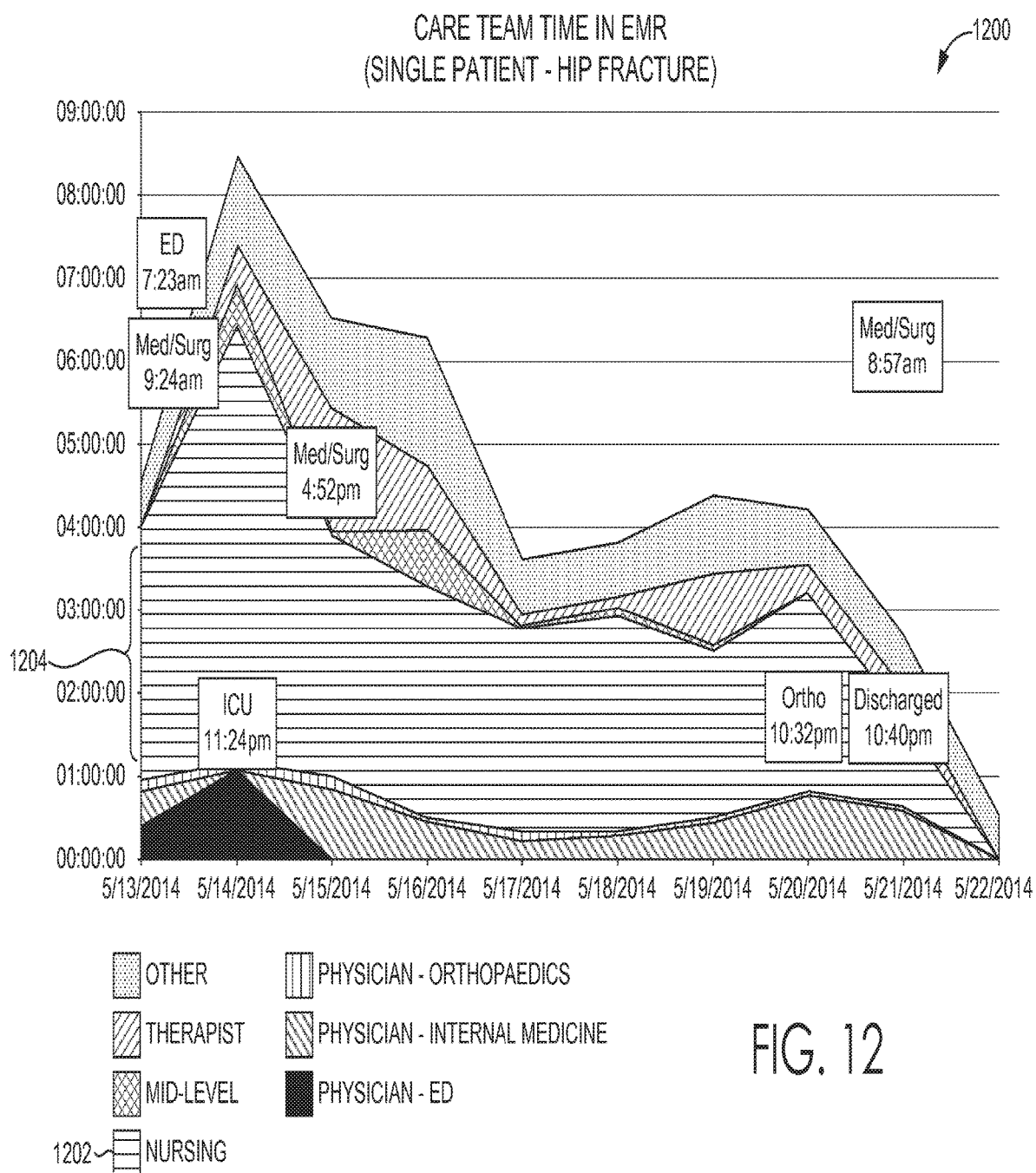
FIG. 12 depicts a per-patient time data summary further segmented to a per-clinician time data level, in accordance with an embodiment of the present invention.

Turning now to FIG. 12, an exemplary GUI 1200 is provided illustrating a time data analysis for a single patient (per-patient time data level) that is further broken down by clinician-type (e.g., nurse, mid-level clinician, therapist, emergency department physician, orthopaedic physician, internal medicine physician, etc.). This is a patient-centric view that illustrates how much time each type of clinician spent in the EMR for this patient. This data may be used to, among other things, identify time data issues (e.g., if a particular clinician or clinician-type is spending too much time in the EMR), identify use (e.g., which clinician-types use the EMR the most through the day so that future innovations/training/configurations may be directed to the use), and identify costs for types of patients. As is noted in FIG. 12, the patient analyzed in this example is a hip fracture patient. All of the time spent in the EMR could be converted to cost (e.g., U.S. dollars) to identify potential time data issues (e.g., times spent in the EMR that are associated with a cost exceeding a predetermined cost threshold). In those situations it may be an issue with how much time is spent in an EMR or it could be identified that rather than EMR modifications, a particular clinician would benefit more from delegation education and handing off some tasks that could be done by other clinicians. For instance, if a physician is spending large amounts of time in an EMR reviewing something that a nurse or other level clinician could handle, the physician may need to pass some of those duties on to increase their own efficiency and reduce cost.

Figure 13:
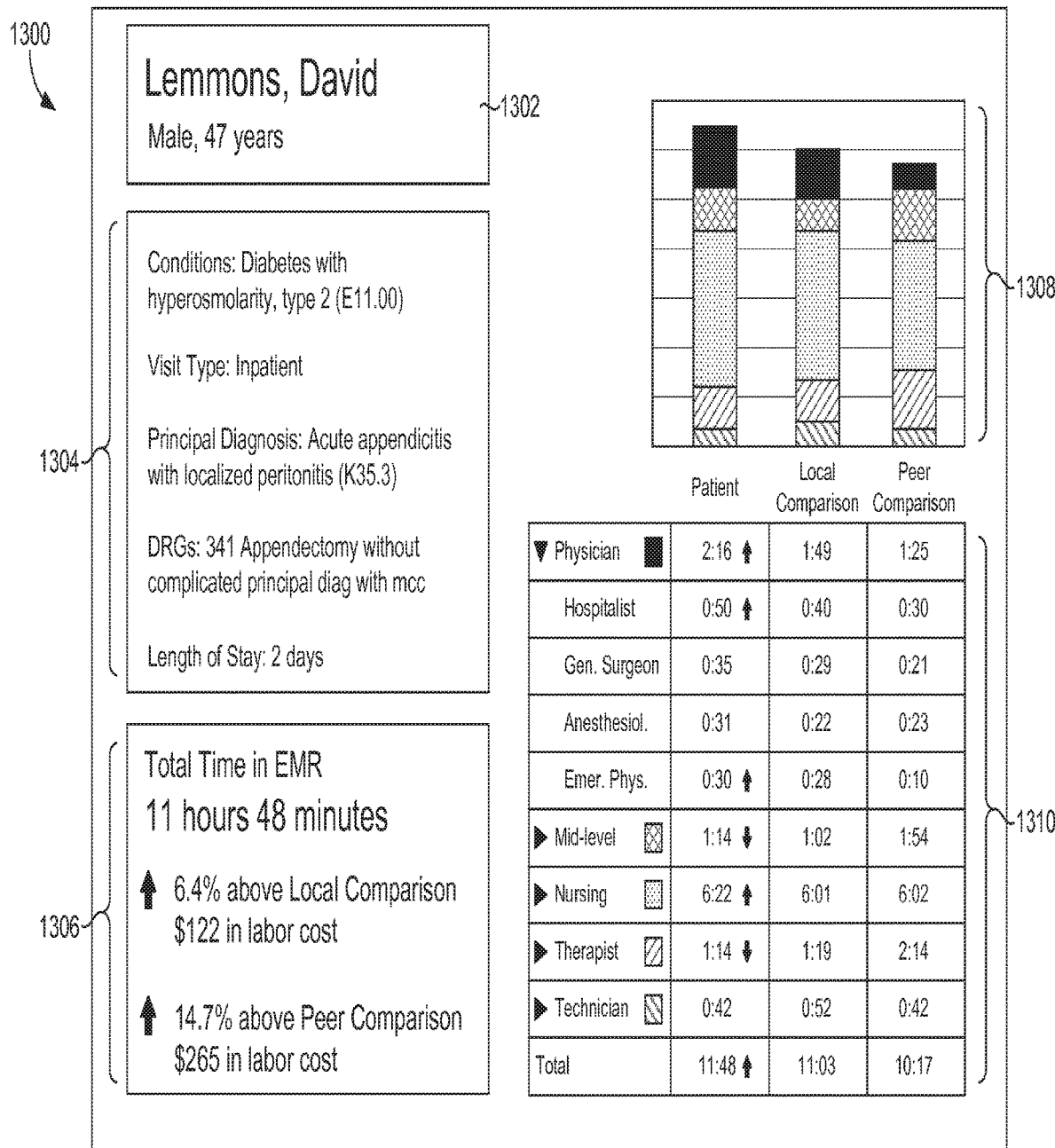
FIG. 13 depicts a per-patient time data GUI, in accordance with an embodiment of the present invention.

Turning now to FIG. 13, an exemplary GUI 1300 is provided that illustrates a per-patient view. The GUI 1300 includes a patient identification area 1302 and a patient information area 1304 that may include a diagnosis, any conditions of the patient, length of stay information, and the like. The GUI 1300 may further include an EMR summary area 1306 that includes a total time in the patient's EMR. The EMR summary area 1306 may include additional information including a local comparison that compares the time spent in the EMR with local facilities and a cost associated with the time spent in the EMR and, also, a peer comparison that compares time spent in the EMR with one or more peers of the facility at which the patient is present. A peer may be a facility that is similar in nature to that which the patient is admitted. For instance, an academic medical center would be a peer of other academic medical centers and not likely a peer of a critical access hospital. The information in the EMR summary area 1306 may also be presented in a graphical EMR summary area 1308, which includes the information of the EMR summary area 1306 but in graphical form instead of textual form. The time data of the EMR summary area 1306 may be further spliced by one or more categories and/or activities. The time data segment area 1310 illustrates said spliced time data. In this example, the time data segment area 1310 includes the time data segmented by clinician-type. For instance, the time data is segmented by physician, mid-level clinician, nurse, therapist, etc. This provides a tool to readily identify clinicians that may be spending too much time in the patient's EMR.

Once collected and analyzed, the communicating component 1412 may be configured for, among other things, communicating one or more of time data, time data analysis results, time data segmentation, one or more recommendations, and the like to a user.

In further embodiments, the system may use time data to predict pathways of a clinician. A pathway, as used herein, refers generally to a path through an EMR or where a user went or goes in an EMR. This pathway prediction may be formulated using a set of time data collected over a predetermined period of time for a clinician. For example, assume time data is collected for Clinician A over a period of one week. Using that data, the system 1400 may identify (using, for example, the identifying component 1408) that Clinician A opens an EMR and goes to an Order Section (for inputting orders) 97% of the time. Using this data, a predicted pathway may be created whereby it is predicted that Clinician A will go directly to the Order Section upon opening the EMR. In embodiments, this predicted pathway may be used to customize Clinician A's experience such that when Clinician A opens an EMR the Order Section will be immediately presented so that Clinician A will not have to navigate to the Order Section. Thus, the Order Section, in this example, may be automatically displayed. Predicted pathways may be useful to increase efficiency. As illustrated in the previous example, an entire step was eliminated for Clinician A when the Order Section is automatically populated. If this is used by the Clinician A 97% of the time (i.e., the 97% of the time when Clinician A desires to go directly to the Order Section) then Clinician A will have saved time throughout the day.

Figure 15:
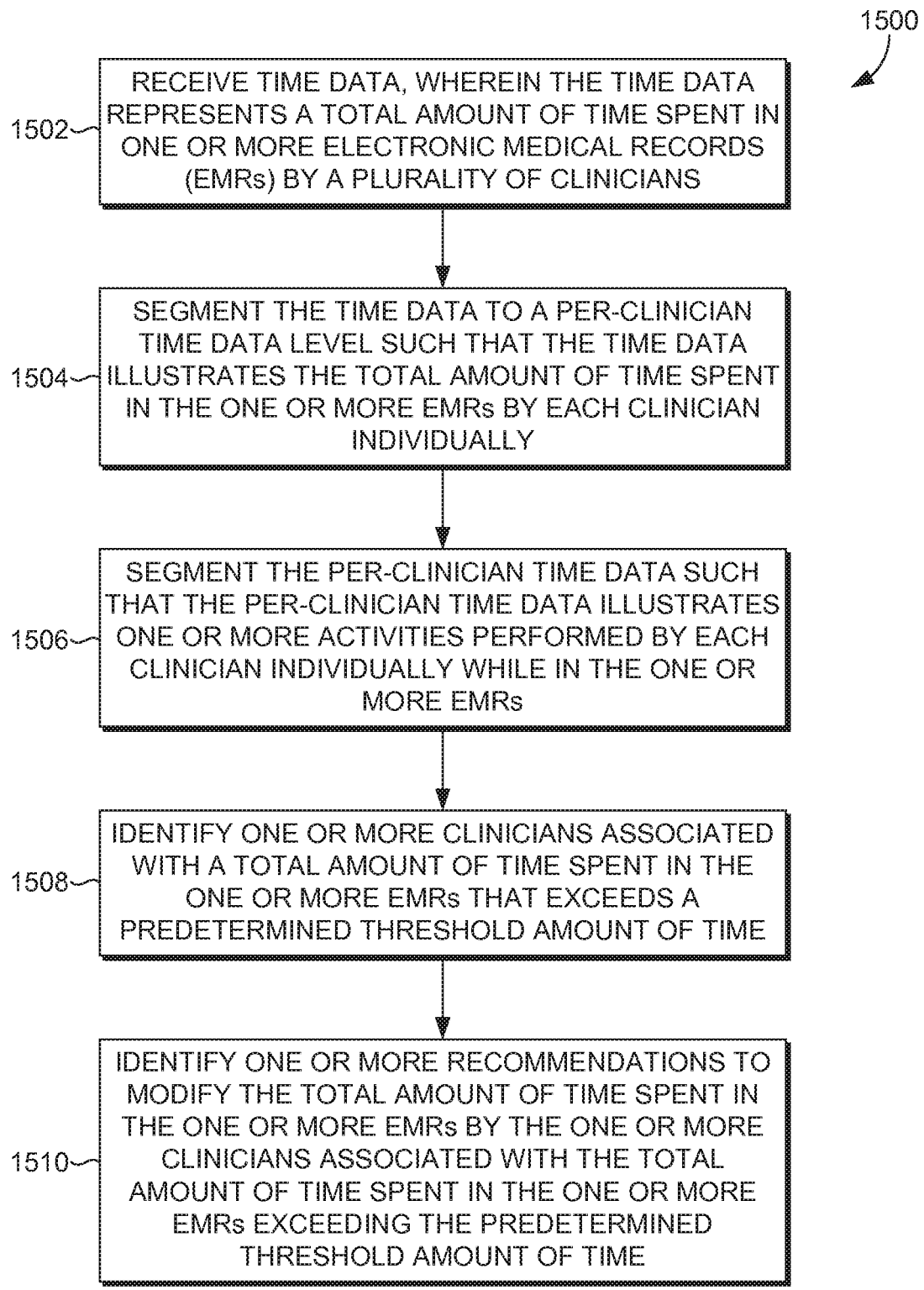
FIG. 15 depicts a flow diagram of an exemplary algorithm for carrying out embodiments of the present invention.

FIG. 15 depicts a flow diagram of a method 1500 for time data analysis, in accordance with an embodiment of the present invention. At block 1502, time data is received. Additional data relevant to time data analysis such as the number of patients seen per clinician may also be received. Time data may represent a total amount of time spent in one or more EMRs by one or more clinicians. At block 1504, the time data is segmented to a per-clinician time data level such that the time data illustrates the total amount of time spent in the one or more EMRs by each clinician individually. The data may be normalized by the number of patients seen to facilitate comparisons between clinicians with different patient volumes. An additional step may be applied to account for varying levels of system functionality used by different clinicians. For example, if Physician A only places 25% of his orders using system functionality, his Orders time in EMR per patient will likely be lower than another provider that places 75% of his orders using the system functionality. To account for this different in adoption of system functionality, the time data may be adjusted to estimate the total time spent in the EMR if the provider were to use the system functionality at 100%. This adjusted time in EMR per patient allows for a comparison of any two clinicians in the system no matter their patient volume or level of adoption of system functionality.

Continuing on with FIG. 15, at block 1506, the per-clinician time data is segmented such that the per-clinician time data illustrates one or more activities performed by each clinician individually while in the one or more EMRs. At block 1508, one or more clinicians associated with a total amount of time spent in the one or more EMRs exceeding a predetermined threshold amount of time is identified. At block 1510, one or more recommendations to modify the total amount of time spent in the one or more EMRs by the one or more clinicians associated with the total amount of time spent in the one or more EMRs exceeding the predetermined threshold amount of time is identified.

Figure 16:
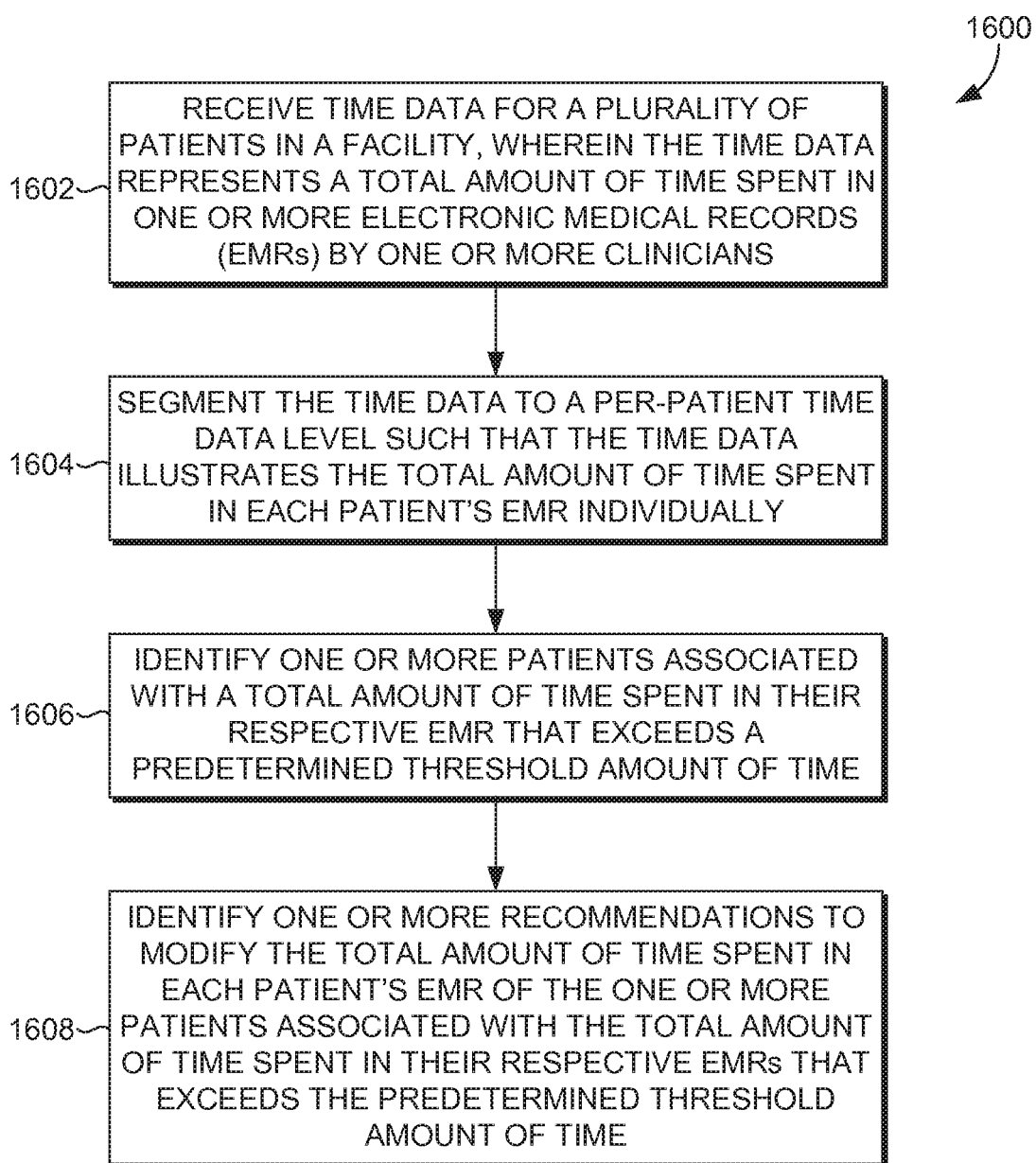
FIG. 16 depicts a flow diagram of an exemplary algorithm for carrying out embodiments of the present invention.

FIG. 16 depicts a flow diagram of another method 1600 for time data analysis, in accordance with an embodiment of the present invention. Initially, at block 1602, time data for a plurality of patients in a facility is received. The time data may represent a total amount of time spent in one or more EMRs by one or more clinicians. At block 1604, the time data is segmented to a per-patient time data level such that the time data illustrates the total amount of time spent in each patient's EMR individually. At block 1606, one or more patients associated with a total amount of time spent in their EMR that exceeds a predetermined threshold amount of time is identified. At block 1608, one or more recommendations to modify the total amount of time spent in each patient's EMR is identified.

Figure 17:
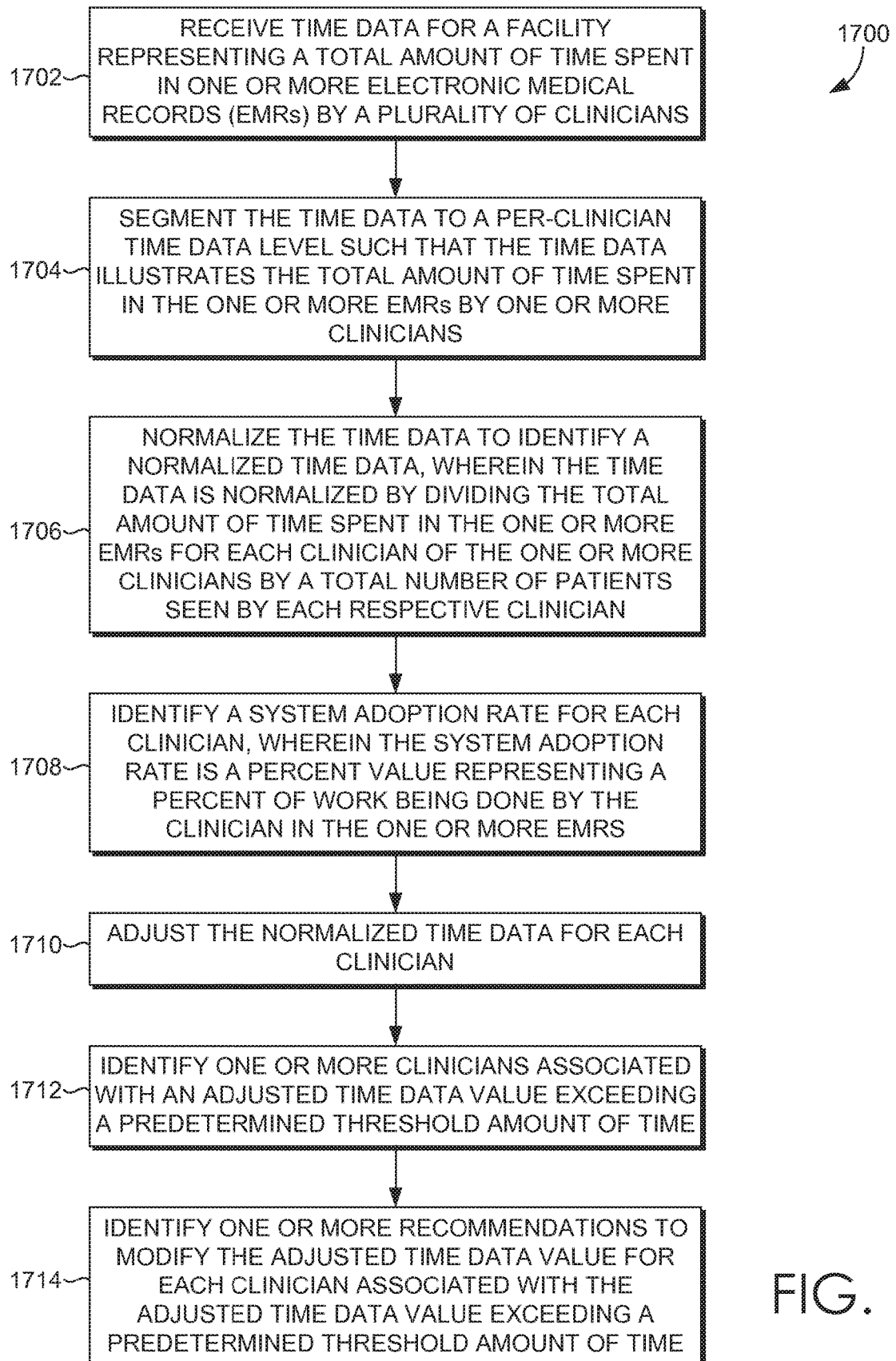
FIG. 17 depicts a flow diagram of an exemplary algorithm for carrying out embodiments of the present invention.

FIG. 17 depicts a flow diagram of another method 1700 for time data analysis, in accordance with an embodiment of the present invention. Initially, at block 1702, time data for a facility is received where the time data represents a total amount of time spent in one or more EMRs by a plurality of clinicians. At block 1704, the time data is segmented to a per-clinician time data level such that the time data illustrates the total amount of time spent in the one or more EMRs by one or more clinicians. At block 1706, the time data is normalized to identify normalized time data for each clinician. The time data may be normalized by dividing the total amount of time spent in the one or more EMRs for each clinician of the one or more clinicians by a total number of patients seen by each respective clinician. At block 1708, a system adoption rate is identified for each clinician. A system adoption rate represents a percent of work being done by the clinician in the EMR indicating, generally, how often the clinician uses the system for activities (such as documentation, ordering, etc.) versus one or more alternatives such as the work being done by another user or being done outside of the system. The system adoption rate is typically a percent value (e.g., 98%, 22.3%, etc.). At block 1810, the normalized time data is adjusted for each clinician. The adjustment step comprises: comparing the system adoption rate for each clinician to a 100% system adoption rate; upon identifying the system adoption rate is lower than 100% system adoption rate, identifying an adjusted time data value for each clinician to adjust the system adoption rate to 100%; and increasing the normalized time data for each clinician to their respective adjusted time data value. As an example, system adoption rates may be lower for clinicians that delegate their EMR duties (e.g., documenting, ordering, etc.) to other clinicians (e.g., nurses, etc.). Those clinicians that delegate, naturally, have a lower percentage of time spent in the EMR than clinicians that access the EMR themselves. At block 1712, one or more clinicians associated with an adjusted time data value exceeding a predetermined threshold amount of time is identified. At block 1714, one or more recommendations to modify the adjusted time data value for each clinician associated with the adjusted time data value exceeding a predetermined threshold amount of time is identified.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A computer system, the system comprising:
    one or more processors; and
    one or more computer storage media having computer-executable instructions embodied thereon that, when executed by the one or more processors, cause the one or more processors to:
    receive time data for a facility representing a total amount of time spent in one or more electronic medical records (EMRs) by a plurality of clinicians;
    segment the time data to a per-clinician time data level such that the time data illustrates the total amount of time spent in the one or more EMRs by one or more clinicians;
    normalize the time data to identify a normalized time data, wherein the time data is normalized by dividing the total amount of time spent in the one or more EMRs for each clinician of the one or more clinicians by a total number of patients seen by each respective clinician;

identify a system adoption rate for each clinician, wherein the system adoption rate is a percent value representing a percent of work being done by the clinician in the EMR;

using the system adoption rate for each clinician, adjust the normalized time data for each clinician, wherein the adjusting comprises:

comparing the system adoption rate for each clinician to a 100% system adoption rate;

upon identifying the system adoption rate is lower than 100% system adoption rate, identifying an adjusted time data value for each clinician to adjust the system adoption rate to 100%; and increasing the normalized time data for each clinician to their respective adjusted time data value;

using the adjusting time data value for each clinician, identify one or more clinicians associated with an adjusted time data value exceeding a predetermined threshold amount of time; and utilizing the per-clinician time data obtained over a predetermined period of time, creating a predicted pathway for a first clinician, the predicted pathway automatically redirecting a default starting view associated with opening the one or more EMRs from a first view to a second view without navigating from the first view to the second view, wherein the first clinician has navigated from the first view of the one or more EMRs to a second view of the one or more EMRs a number of times greater than a predetermined threshold.

2. The system of claim 1, wherein the system adoption rate is below 100% when a first clinician's access to an EMR is performed by a second clinician.

3. The system of claim 1, wherein the one or more processors monitor updated time data of the one or more clinicians.

4. The system of claim 1, wherein the one or more processors:

receive the updated time data subsequent to implementation of the one or more recommendations;

compare the updated time data to a predicted time data for the per-clinician time data level; and based on the comparison, recommend an additional modification if the updated time data for the per-clinician time data level still exceeds the predetermined threshold amount of time.

5. The system of claim 1, wherein the one or more processors associate each clinician with a cost.

6. A computerized method, carried out by at least one computer processing component, the method comprising:

receiving time data for a facility representing a total amount of time spent in one or more electronic medical records (EMRs) by a plurality of clinicians;

segmenting the time data to a per-clinician time data level such that the time data illustrates the total amount of time spent in the one or more EMRs by one or more clinicians;

normalizing the time data to identify a normalized time data, wherein the time data is normalized by dividing the total amount of time spent in the one or more EMRs for each clinician of the one or more clinicians by a total number of patients seen by each respective clinician;

identifying a system adoption rate for each clinician, wherein the system adoption rate is a percent value representing a percent of work being done by the clinician in the EMR;

using the system adoption rate for each clinician, adjusting the normalized time data for each clinician, wherein the adjusting comprises:

comparing the system adoption rate for each clinician to a 100% system adoption rate;

upon identifying the system adoption rate is lower than 100% system adoption rate, identifying an adjusted time data value for each clinician to adjust the system adoption rate to 100%; and increasing the normalized time data for each clinician to their respective adjusted time data value;

using the adjusted time data value for each clinician, identifying one or more clinicians associated with an adjusted time data value exceeding a predetermined threshold amount of time; and utilizing the per-clinician time data obtained over a predetermined period of time, creating a predicted pathway for a first clinician, the predicted pathway automatically redirecting a default starting view associated with opening the one or more EMRs from a first view to a second view without having to navigate from the first view to the second view, wherein the first clinician has navigated from the first view of the one or more EMRs to a second view of the one or more EMRs a number of times greater than a predetermined threshold.

7. The method of claim 6, wherein the total amount of time spent in the one or more EMRs represents active time, wherein active time includes time spent performing one or more activities associated with an active indication having a time interval between a subsequent active indication that is no greater than a predefined time interval.

8. The method of claim 7, wherein the active indication includes one or more of a keystroke, a mouse click, or mouse miles.

9. The method of claim 7, wherein active time is distinguished from inactive time using one or more timers for measuring a time interval between two or more active indications.

10. The method of claim 9, wherein the one or more timers collect metadata including a time stamp for an activity, a description of the activity, and one or more tags for data segmentation.

11. The method of claim 10, wherein time data is segmented based on one or more of area of specialty, location, clinician, patient, or activity.

12. The method of claim 10, wherein the one or more tags include a clinician tag, a patient tag, a location tag, and an area of specialty tag.

13. The method of claim 6, wherein the time data is collected for a predetermined time period.

14. The method of claim 6, wherein the automatically redirecting a default starting view associated with opening the one or more EMRs from a first view to a second view is done without first navigating to the first view.

15. The method of claim 6, further comprising identifying a portion of the time data is that collected from one or more clinicians during outside hours, wherein outside hours are outside of a designated shift of hours.

16. One or more computer storage media having computer-executable instructions embodied thereon that, when executed, facilitate a method of time data analysis, the method comprising:

receiving time data for a facility representing a total amount of time spent in one or more electronic medical records (EMRs) by a plurality of clinicians;

segmenting the time data to a per-clinician time data level such that the time data illustrates the total amount of time spent in the one or more EMRs by one or more clinicians;

normalizing the time data to identify a normalized time data, wherein the time data is normalized by dividing the total amount of time spent in the one or more EMRs for each clinician of the one or more clinicians by a total number of patients seen by each respective clinician;

identifying a system adoption rate for each clinician, wherein the system adoption rate is a percent value representing a percent of work being done by the clinician in the EMR;

using the system adoption rate for each clinician, adjusting the normalized time data for each clinician, wherein the adjusting comprises:
  comparing the system adoption rate for each clinician to a 100% system adoption rate;
  upon identifying the system adoption rate is lower than 100% system adoption rate, identifying an adjusted time data value for each clinician to adjust the system adoption rate to 100%; and
  increasing the normalized time data for each clinician to their respective adjusted time data value;

using the adjusted time data value for each clinician, identifying one or more clinicians associated with an adjusted time data value exceeding a predetermined threshold amount of time; and utilizing the per-clinician time data obtained over a predetermined period of time, creating a predicted pathway for a first clinician, the predicted pathway automatically redirecting a default starting view associated with opening the one or more EMRs from a first view to a second view without having to navigate from the first view to the second view, wherein the first clinician has navigated from the first view of the one or more EMRs to a second view of the one or more EMRs a number of times greater than a predetermined threshold.

17. The media of claim 16, wherein the time data is collected for a predetermined time period.

18. The media of claim 16, further comprising segmenting the per-patient time data into one or more activities performed in each patient's EMR on a per-patient basis.

19. The media of claim 18, further comprising associating each activity of the one or more activities performed in each patient's EMR with a cost.

20. The media of claim 16, further comprising associating each patient with a cost based on the total amount of time spent in their respective EMRs exceeding the predetermined threshold of time.

* * * * *